United States Patent [19]

Tewes et al.

[11] 4,317,366

[45] Mar. 2, 1982

[54] METHOD AND SYSTEM FOR MEASURING TEMPERATURES IN COMBUSTION CHAMBERS

[75] Inventors: Giesbert Tewes; Henner Schmidt-Traub, both of Essen, Fed. Rep. of Germany

[73] Assignee: Krupp-Koppers GmbH, Essen, Fed. Rep. of Germany

[21] Appl. No.: 103,534

[22] Filed: Dec. 14, 1979

[30] Foreign Application Priority Data

Dec. 18, 1978 [DE] Fed. Rep. of Germany ....... 2854577

[51] Int. Cl.$^3$ .............................................. G01K 3/08
[52] U.S. Cl. ................................................ 73/339 A
[58] Field of Search ......................... 73/339 A, 30, 645

[56] References Cited

U.S. PATENT DOCUMENTS

| | | | |
|---|---|---|---|
| 2,871,348 | 1/1959 | Hutchinson et al. | 324/81 UX |
| 3,604,252 | 9/1971 | Becken | 73/339 A X |
| 3,706,227 | 12/1972 | Gottron et al. | 73/339 A |
| 3,885,436 | 5/1975 | Meyer | 73/339 A |
| 4,020,693 | 5/1977 | Ahlgren et al. | 73/339 A |

Primary Examiner—Jerry W. Myracle
Attorney, Agent, or Firm—Michael J. Striker

[57] ABSTRACT

The interior space of a combustion chamber, boiler, or other such gas-filled chamber exhibits an acoustic response spectrum to acoustic energy excitation which includes plural maxima attributable to acoustic natural-vibration frequencies. The frequencies of these natural vibrations are dependent upon both the interior temperature of the chamber and also upon the normality or molarity of the gaseous contents of the chamber. One of these two variables, i.e., temperatures or else normality or molarity, is measured by conventional devices. The other variable is then measured using a pressure transducer generating an electrical signal indicative of the chamber interior's acoustic response spectrum, the transducer output signal being applied to a discriminator circuit which develops a measurement signal indicative of the value of the variable being measured. In this way, interior temperature can be continuously monitored by acoustic devices with high accuracy.

6 Claims, 1 Drawing Figure

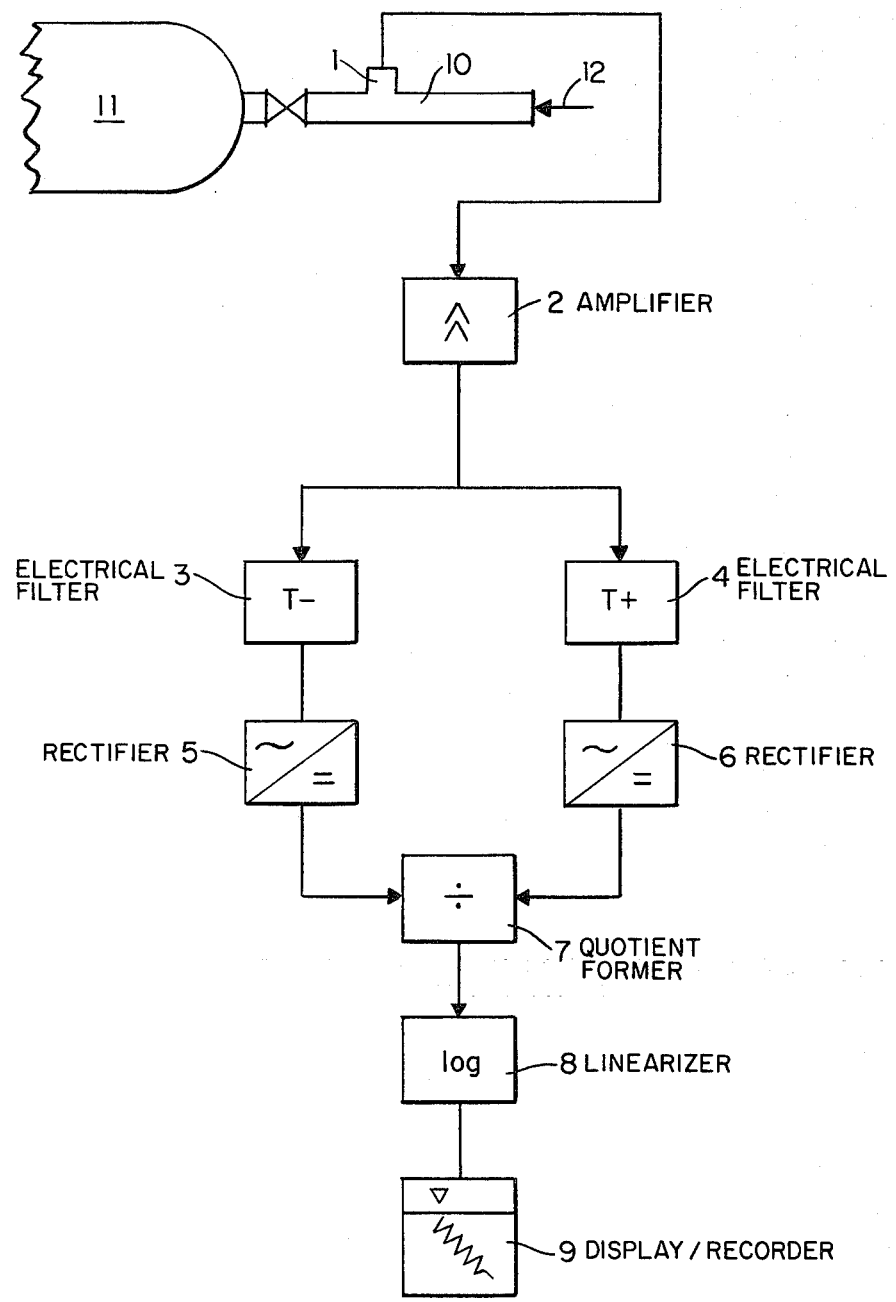

METHOD AND SYSTEM FOR MEASURING TEMPERATURES IN COMBUSTION CHAMBERS

BACKGROUND OF THE INVENTION

1. Field of the Invention

This invention generally relates to the measurement of elevated temperatures in gas-filled chambers and specifically to the measurement of the elevated temperatures of combustion chambers and the like by acoustic means.

2. Description of the Prior Art

Continual measurement of high temperature in combustion chambers and reactors containing aggressive gases or gases which include a high fraction of solids presents enormous difficulties when use is made of conventional measuring techniques of the type utilizing thermoelements or optical devices. In the case of thermoelements, the major sources of difficulty are corrosion and the deposition of dirt on the thermoelements; in the case of optical devices, the major sources of difficulty are dirt, clouds of solids swirling in front of the optical devices, the formation of drops of non-transparent liquid on the optical devices, and direct exposure to flame. As a result, the primary detectors or transducers used in such techniques have only a relatively short service life and provide a temperature indication of somewhat uncertain accuracy.

It is accordingly a general object of the invention to provide a novel temperature-measurement technique, for use in the continual monitoring of the operation of combustion chambers, e.g., coking ovens, or reactors, e.g., coal gasification reactors, which is free of the disadvantages referred to above.

SUMMARY OF THE INVENTION

The invention exploits the temperature dependence of the acoustic characteristics of the interior of combustion chambers or other gas-filled chamber. In accordance with one concept of the invention, the temperature in the interior of the chamber of interest is ascertained from the spectrum of the acoustic response of the chamber's interior, the acoustic pressure within the chamber being detected by a pressure transducer, and there then being ascertained from the maxima of the acoustic pressure spectrum one or more resonant frequencies which are utilized as a measure of the average temperature in the chamber's interior.

According to a further concept of the invention, one or more resonant frequencies characteristic of the chamber's acoustic response are each measured by means of a respective pair of electrical filters, the two filters of each such pair being detuned, in opposite respective directions, from the respective resonant frequency to be measured, i.e., such that one filter of the pair has its frequency of maximum transmission lower than and the other higher than the respective resonant frequency. The output signals from the two electrical filters of each such pair of filters are then combined by a calculating circuit to yield a temperature-dependent signal.

According to a further concept of the invention, the requisite acoustic excitation of the interior of the chamber of interest can be established by means of an acoustic energy source specially provided within the chamber interior for this purpose.

According to a related concept of the invention, if the temperature in the chamber interior is additionally ascertained by some other technique, then the acoustic response measured in accordance with the present invention can also be used to develop a signal which serves to indicate the average normality or the average molarity of the gas in the chamber interior, with the acoustic excitation of the chamber interior being effected, if necessary, by means of an acoustic energy source specially provided for this purpose.

These and other features of the present invention will be more completely disclosed and described in the following specification, the accompanying drawing and the appended claims.

BRIEF DESCRIPTION OF THE DRAWING

The sole drawing is a schematic block diagram of the apparatus usage sequence in the method of the system of the invention.

DETAILED DESCRIPTION

The volume of gas in the interior of a combustion chamber or of a reactor constitutes, in a manner similar to the column of air in an organ pipe, a system capable of exhibiting a resonant response to excitation, and having certain definite acoustic resonances at discrete respective resonant frequencies. These resonant frequencies are mainly determined by the geometry and dimensions, $L_i$, of the chamber interior and by the velocity of sound in the particular gas accommodated in the chamber interior. Due to the dependence of the velocity of sound upon the temperature T of the gas involved, the following relationship exists between the resonant frequencies $f_i$ present and the temperature T:

$$f_i \sim \frac{1}{L_i}\sqrt{\frac{T}{\rho\mu}}$$

wherein $\rho\mu$ signifies the normality of the gas involved, and i is an index which characterizes the correlation between the fundamental resonant frequency of the acoustic response, on the one hand, and, on the other hand, the geometry and dimensions, $L_i$, of the chamber interior.

If such a system is excited by means of broadband acoustic noise such as is present during actual practice in consequence of ordinary gas flow noise and flame noise, those spectral components of the excitation noise which are located in the vicinities of the resonant frequencies present are emphasized, due to resonance rise, compared to the remainder of the spectrum of the noise energy. As a result, clear maxima can be observed in the acoustic pressure spectrum of the combustion-chamber interior at the characteristic or resonant frequencies of the chamber interior. Accordingly, it becomes possible to ascertain the average temperature in the chamber interior, in reliance upon the relationship presented above, by consideration of a few of the characteristic frequencies of the acoustic spectrum of the combustion chamber or reactor, if the normality of the gas in the chamber interior is known.

In terms of implementing equipment, use is preferably made of an electrical signal-generating pressure transducer at least communicating with the interior of the chamber of interest, with an amplifier being connected to the output of the pressure transducer and a discriminator circuit connected to the output of the amplifier, the output signal of the measuring system being used to drive a digital or analog indicator and/or a pen or other such recorder.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

The equipment set-up depicted in the drawing, for implementation of the invention, includes a pressure transducer 1 which senses the acoustic pressure in the interior 11 of the reactor of interest and produces a corresponding electrical signal, which is amplified by an amplifier 2. The amplified signal is applied to two electrical filters 3 and 4. The bandpass of the two filters 3, 4 are respectively lower than and higher than the expected frequency location of the particular temperature-dependent resonant frequency to be measured, i.e., of the plural resonant frequencies which the acoustic response spectrum of the reactor interior will in general exhibit, the two filters 3, 4 being used to ascertain the exact frequency location of the particular temperature-dependent resonant frequency of interest in a manner analogous to a communications-technology differential discriminator. The output signals from the two filters 3, 4 are applied, via respective rectifiers 5 and 6, to the two inputs of a quotient-forming stage 7, the output signal of which is applied to the input of a logarithmic stage 8 to linearize the signal in question, i.e., so that the output signal from stage 8 be proportional to temperature. The linearized temperature-representing signal is then applied to a display and/or recorder stage 9, for a visible display and/or visible record of temperature. The interior 11 of the chamber of interest is in pressure-transmitting communication with the pressure transducer 1 through the intermediary of a sound-absorbing probe 10, the latter being flushed by nitrogen introduced at 12.

The operativeness of the inventive technique for practical use was investigated using a coal-gasification reactor of industrial dimensions, this being a reactor of a type which poses enormous difficulties for the continuous monitoring of internal temperature by conventional means, due to the high fraction of coal dust and the aggressive properties of the liquid slag involved. The measuring equipment employed, in accordance with the principle described above, was performed using bandpass filters such as customarily used in acoustic-measurement technology, and yielded a temperature sensitivity of about 6 dB per 100° K. at an absolute temperature of about 1650° K. The measuring system responded to changes of reactor operation with a response time of less than 15 seconds and would assume a new steady-state within about one minute.

This investigation revealed the following advantages, in addition to good sensitivity values and short response times: The measuring apparatus employed can be assembled from relatively inexpensive, commercially available components. The primary transducer of the system can be very easily connected to the interior of the chamber of interest in such a manner that it be subjected to neither deleterious temperatures nor to aggressive media within the chamber interior. To protect the transducer from contamination by deposits, flushing with a relatively low flow of nitrogen is sufficient. The output signal of the measurement system serves as a measure of the average temperature of the chamber interior, i.e., averaged over the chamber's interior volume, but its accuracy and reliability are not affected by the heat radiating from flames in the reactor nor by the absorption of radiant energy by suspended particulate matter in the reactor.

In view of these advantages, the inventive technique is extremely well suited for temperature measurements in gas-filled chambers of high interior temperature and/or chambers containing aggressive or highly contaminated atmospheres, such as: industrial combustion chambers, boilers and furnaces; coke-oven heating flues; and coal gasification reactors.

The inventive method is not exclusively limited to the measurement of temperature. Inasmuch as the velocity of sound in a gas is dependent upon both the temperature and the normality or molarity of the gas involved, it is alternatively contemplated to utilize the inventive method to measure the average normality or molarity of the gas in a gas-filled chamber, the average temperature of the chamber interior then being ascertained by some other method, e.g., any of various conventional methods.

It will be understood that each of the elements described above, or two or more together, may also find a useful application in other types of procedures and equipment set-ups, differing from the types described above.

While the invention has been illustrated and described as embodied in the measurement of temperature, or of the normality or molarity of gases, in the interior of a combustion chamber, or the like, it is not intended to be limited to the details shown, since various modifications and structural changes may be made without departing in any way from the spirit of the present invention.

According to the provisions of the patent statutes, the principle, preferred arrangement and mode of operation of the present invention have been explained and its best embodiment has been illustrated and described. However, it is to be understood that, within the scope of the appended claims, the present invention may be practiced otherwise than as specifically illustrated and described.

What is claimed is:

1. A method of measuring the spatially averaged temperature in the interior of a combustion chamber, or other such gas-filled chamber, by reliance upon the temperature dependence of the acoustic properties of the interior of such chamber, comprising:
    (a) imposing a pressure transducer into said chamber;
    (b) sensing the spectrum of the acoustic response of the interior of said chamber to acoustic excitation produced by gas flow noise and flame noise in said chamber, with said transducer;
    (c) developing, from at least one maximum of said spectrum, an indication of the frequency of at least one acoustic natural vibration of said interior of said chamber; and
    (d) developing, from said indication of said frequency, an indication of the spatially averaged temperature within said interior of said chamber.

2. A method as described in claim 1 wherein said developing of a said indication of said frequency of said at least one acoustic natural vibration of said interior of said chamber comprises:
    (a) employing said transducer to generate an electrical signal;

(b) applying said electrical signal to a pair of electrical filters which are associated with the frequency of said at least one natural vibration, each of said pair of filters having bandpass frequency ranges respectively lower than, and higher than, the temperature-dependent frequency range within which the respective said natural vibration frequency occurs;

and wherein said developing of a said indication of such spatially averaged temperature within said interior with said chamber comprises (c) applying the output signals of said pair of filters to a means for developing a temperature-indicating signal indicative of said spatially averaged temperature within said interior of said chamber.

3. A method as described in claim 2 further comprising employing a source of acoustic energy to acoustically excite said interior of said chamber.

4. A method as described in claim 1 further comprising employing a source of acoustic energy to acoustically excite said interior of said chamber.

5. A method of measuring the normality and molarity of the gaseous contents of a combustion chamber, or other such gas filled chamber, by relying on the normality-dependence and molarity dependence of the acoustic properties of said combustion chamber, comprising (a) applying a pressure transducer to the interior of said combustion chamber, to sense the spectrum of the acoustic response of said interior of said combustion chamber to acoustic excitation;

(b) developing, from at least one maximum of said spectrum, an indication of the frequency of at least one acoustic natural vibration of said interior of said combustion chamber;

(c) using said frequency indication to form an indication of the normality and molarity of the gaseous contents within said interior of said combustion chamber.

6. In combination with a combustion chamber or other such gas-filled chamber, a system for measuring the temperature or the normality and molarity of the interior space of the gas-filled chamber, said measuring system comprising:

(a) a pressure transducer arranged to generate an electrical signal indicative of the spectrum of the acoustic response of the interior of said chamber to acoustic excitation produced by gas flow noise and flame noise in said chamber;

(b) means for amplifying said electrical signal;

(c) means for receiving said amplified electrical signal and converting into an output signal generally dependent upon the frequency of an acoustic natural vibration of said interior of said chamber; and (d) means for effecting a visible display directly related to said output signal.

* * * * *